United States Patent
Panken et al.

(10) Patent No.: US 12,011,287 B2
(45) Date of Patent: Jun. 18, 2024

(54) MEDICAL DEVICE USING SPECTRAL ACTIVITY PROCESSING

(71) Applicant: Medtronic, Inc., Minneapolis, MN (US)

(72) Inventors: Eric J. Panken, Edina, MN (US); Mandla Shongwe, Brooklyn Park, MN (US)

(73) Assignee: Medtronic, Inc., Minneapolis, MN (US)

(*) Notice: Subject to any disclaimer, the term of this patent is extended or adjusted under 35 U.S.C. 154(b) by 187 days.

(21) Appl. No.: 17/183,398

(22) Filed: Feb. 24, 2021

(65) Prior Publication Data
US 2022/0265209 A1 Aug. 25, 2022

(51) Int. Cl.
*A61B 5/00* (2006.01)
*A61B 5/11* (2006.01)

(52) U.S. Cl.
CPC .......... *A61B 5/4836* (2013.01); *A61B 5/0002* (2013.01); *A61B 5/1118* (2013.01); *A61B 5/1123* (2013.01); *A61B 5/7257* (2013.01); *A61B 2562/0219* (2013.01)

(58) Field of Classification Search
CPC ... A61B 5/4836; A61B 5/0002; A61B 5/1118; A61B 5/1123; A61B 5/7257; A61B 2562/0219; A61N 1/36003; A61N 1/36067; A61N 1/36128; A61N 1/36542
See application file for complete search history.

(56) References Cited

U.S. PATENT DOCUMENTS

| | | | |
|---|---|---|---|
| 10,381,109 B2 | 8/2019 | Hong et al. | |
| 10,729,332 B2 | 8/2020 | Heneghan et al. | |
| 10,773,084 B2 | 9/2020 | Grill et al. | |
| 2005/0060001 A1 | 3/2005 | Singhal et al. | |
| 2008/0300649 A1 | 12/2008 | Gerber et al. | |

(Continued)

FOREIGN PATENT DOCUMENTS

EP 2945691 B1 3/2019

OTHER PUBLICATIONS

Erdaş, Ç. Berke, et al. "Integrating features for accelerometer-based activity recognition." Procedia Computer Science 98: 522-527. (Year: 2016).*

(Continued)

*Primary Examiner* — Alex M Valvis
*Assistant Examiner* — Nidhi N Patel
(74) *Attorney, Agent, or Firm* — Shumaker & Sieffert, P.A.

(57) ABSTRACT

A system for providing stimulation to a patient includes one or more processors implemented in circuitry and one or more accelerometers configured to generate one or more accelerometer signals. The one or more processors are configured to determine accelerometer information for a medical device associated with the patient based on the one or more accelerometer signals and convert the accelerometer information into frequency domain coefficients. The one or more processors are further configured to determine an activity level for the patient based on the frequency domain coefficients and determine one or more stimulation parameters based on the activity level. The one or more processors are further configured to output electrical stimulation to the patient based on the one or more stimulation parameters.

12 Claims, 7 Drawing Sheets

(56) References Cited

U.S. PATENT DOCUMENTS

| | | | |
|---|---|---|---|
| 2009/0082691 | A1 | 3/2009 | Denison et al. |
| 2013/0231715 | A1 | 9/2013 | Grill, Jr. et al. |
| 2013/0345773 | A1 | 12/2013 | Grill et al. |
| 2014/0303523 | A1 | 10/2014 | Hong et al. |
| 2015/0117645 | A1 | 4/2015 | Carlson et al. |
| 2016/0317097 | A1* | 11/2016 | Adams .................. G16H 50/20 |
| 2016/0361021 | A1 | 12/2016 | Salehizadeh et al. |
| 2021/0022676 | A1* | 1/2021 | Lamego ............. A61B 5/02055 |
| 2021/0402185 | A1* | 12/2021 | Van den Heuvel .......................... A61N 1/36038 |

OTHER PUBLICATIONS

International Search Report and Written Opinion of International Application No. PCT/US2022/016273, dated May 31, 2022, 12 pp.

* cited by examiner

MEDICAL DEVICE USING SPECTRAL ACTIVITY PROCESSING

TECHNICAL FIELD

This disclosure generally relates to medical devices, and more specifically, electrical stimulation.

BACKGROUND

Medical devices (e.g., an implantable medical device or an external medical device) may include electrical stimulation devices, drug pumps, insulin pumps, or cardiac stimulation devices. Electrical stimulation devices, for example, neurostimulators or neurostimulation devices, may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads, positioned proximate to target locations associated with the brain, the spinal cord, pelvic nerves, tibial nerves, peripheral nerves, the gastrointestinal tract, or elsewhere within a patient. Stimulation proximate the spinal cord, proximate the sacral nerve, within the brain, and proximate peripheral nerves is often referred to as spinal cord stimulation (SCS), sacral neuromodulation (SNM), deep brain stimulation (DBS), and peripheral nerve stimulation (PNS), respectively.

SUMMARY

In general, the disclosure describes techniques for programming medical devices, such as implantable medical devices, to apply one or more stimulation parameters (e.g., neurostimulation parameters). For example, the techniques may include selecting one or more stimulation parameters based on an activity level of a patient. In some examples, the techniques may be used to manually, automatically, or semi-automatically select one or more stimulation parameters such as, for example, electrode selections, combinations and polarities, stimulation amplitude, pulse width, pulse rate, or cycling, adjustments to such parameters, and/or programs specifying such parameters, for delivery of stimulation by a medical device, such as, for example, an implantable medical device (IMD).

The techniques of this disclosure, in some examples, include a system configured to determine an activity level for the patient based on frequency domain coefficients. For example, the system may convert the accelerometer information into frequency domain coefficients using a fast Fourier transform (FFT). Converting the accelerometer information into the frequency domain may allow for a more accurate and/or simplified processing of accelerometer information to determine an activity level compared to systems that only rely on a time domain representation of accelerometer data. For example, the system may filter out one or more frequency domain coefficients that are outside of a range of frequency. For instance, the system may apply a band pass filter of between 0.75 Hz to 10 Hz to filter out frequency domain coefficients that correspond to acceleration by a car. In this way, the system may determine an activity level of a patient that is more accurate compared to systems relying only on a time domain representation of accelerometer data. Additionally, higher accuracy in determining an activity level of the patient may allow the system to more accurately determine stimulation parameters (e.g., a program), which may improve a therapy provided to the patient when providing electrical stimulation to the patient compared to systems relying only on a time domain representation of accelerometer data.

In one example, a system for providing stimulation to a patient includes one or more processors implemented in circuitry and one or more accelerometers configured to generate one or more accelerometer signals. The one or more processors are configured to determine accelerometer information for a medical device associated with the patient based on the one or more accelerometer signals and convert the accelerometer information into frequency domain coefficients. The one or more processors are further configured to determine an activity level for the patient based on the frequency domain coefficients and determine one or more stimulation parameters based on the activity level. The one or more processors are further configured to output electrical stimulation to the patient based on the one or more stimulation parameters.

In another example, a method for providing stimulation to a patient includes determining, by one or more processors, accelerometer information for a medical device associated with the patient based on one or more accelerometer signals generated by one or more accelerometers and converting, by the one or more processors, the accelerometer information into frequency domain coefficients. The method further includes determining, by the one or more processors, an activity level for the patient based on the frequency domain coefficients and determining, by the one or more processors, one or more stimulation parameters based on the activity level. The method further includes outputting, by the one or more processors, electrical stimulation to the patient based on the one or more stimulation parameters.

In one example, a medical device for providing stimulation to a patient includes one or more processors implemented in circuitry, a frequency domain unit implemented in the circuitry, and one or more accelerometers configured to generate one or more accelerometer signals. The one or more processors are configured to determine accelerometer information based on the one or more accelerometer signals. The frequency domain unit is configured to convert the accelerometer information into frequency domain coefficients. The one or more processors are further configured to determine an activity level for the patient based on the frequency domain coefficients, determine one or more stimulation parameters based on the activity level, and output electrical stimulation to the patient based on the one or more stimulation parameters.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
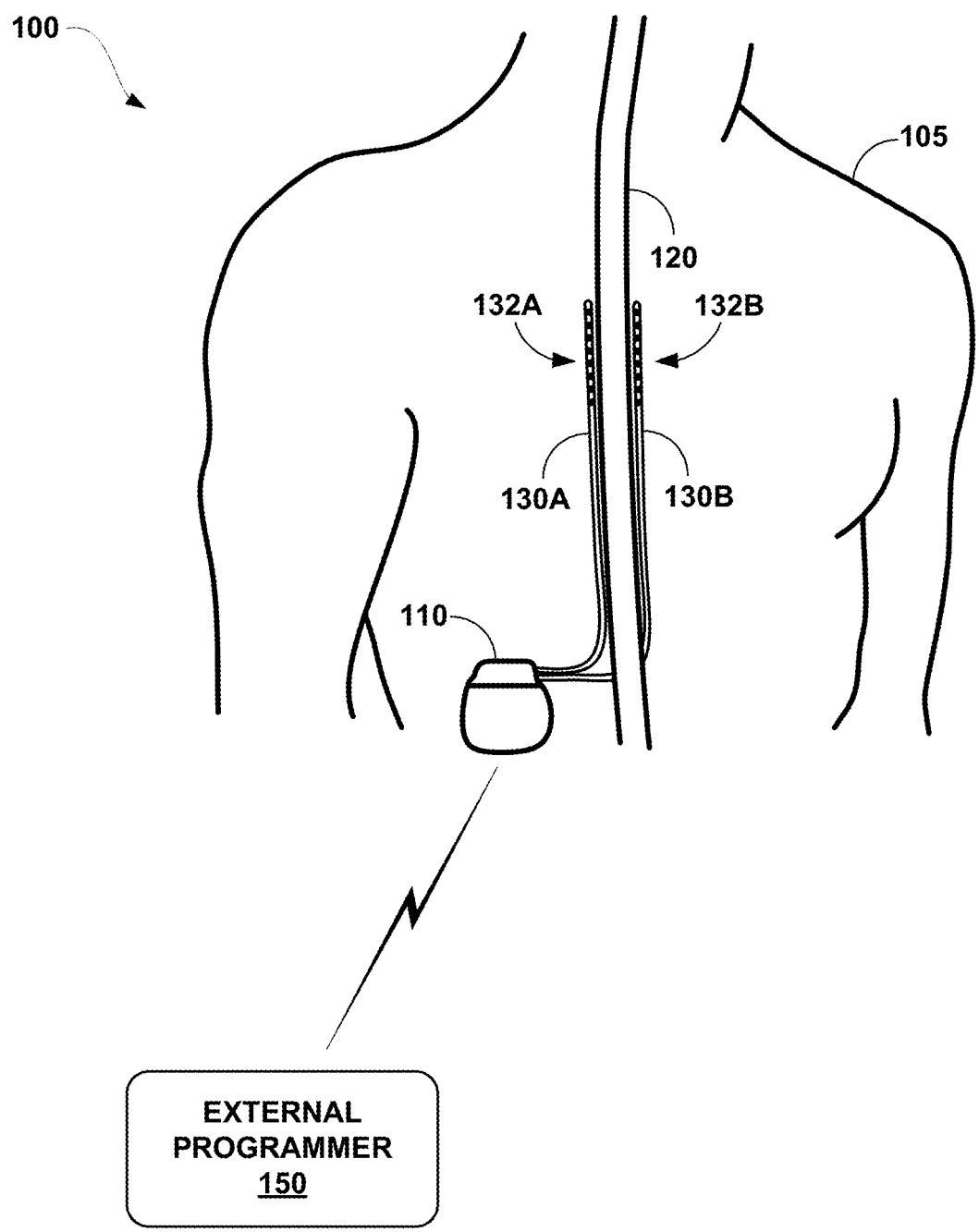
FIG. 1 is a conceptual diagram illustrating an example system that includes an implantable medical device (IMD) in the form of a stimulation device configured to deliver spinal cord stimulation (SCS) and an external programmer, in accordance with one or more techniques of this disclosure.

Efficacy of stimulation (e.g., neurostimulation) in eliminating or alleviating symptoms, preventing, or delaying onset or progression of aspects of, or restoring functions impaired or diminished by a disease, disorder, syndrome, or injury, may vary according to the parameters used to deliver the stimulation to a patient. Selection of electrode positions relative to a neural target, as one example, can elicit a desired response to the stimulation. Delivering stimulation with different stimulation parameters, such as different electrodes, electrode combinations and/or polarities, or different stimulation amplitudes, pulse widths, pulse rates, or cycling can result in differences in efficacy for a variety of therapies such as, for example, spinal cord stimulation (SCS) to relieve pain or restore physical function or control in the case of spinal cord injury or degeneration.

A medical device may deliver stimulation to a patient using one or more "programs," where each program may indicate one or more stimulation parameters such as, for example, electrode selections, combinations and polarities, stimulation amplitude, pulse width, pulse rate, or cycling, adjustments to such parameters, and/or programs specifying such parameters, for delivery of stimulation by a medical device, such as, for example, an implantable medical device (IMD). For example, the medical device may store N groups of programs, each providing M programs defining different sets of stimulation parameters, wherein N and M may be the same or different. In one example, the medical device may have N=3 groups and each group may include up to M=4 programs. For example, within a group of programs, a first program may provide a therapy for leg pain, a second program may provide a first therapy for back pain, and a third program may provide a second therapy for the back pain. In this example, the medical device may provide stimulation using both the first program and one of the second program or the third program. In this way, a single medical device may provide therapy for multiple symptoms (e.g., leg pain and back pain). In some examples, a medical device may deliver therapy according to a plurality of programs in a group of programs, e.g., on a time-interleaved basis with one another.

An external programmer may configure a medical device with different groups of programs, and different programs within a group of programs. For example, a patient, caretaker, or health professional may generate, with the external programmer, a new program or program group to improve a therapy. In this example, the external programmer may configure the medical device with new program(s) and set the stimulation to apply the new program(s) to provide stimulation to provide the improved therapy to the patient. In some examples, the external programmer may be configured to automatically, or semi-automatically generate the new program to improve therapy, e.g., in response to an event, such as a sensed condition. For example, in response to a change from a first activity (e.g., a patient sitting) to a second activity (e.g., walking), the external programmer may generate a new program that may provide more effective therapy (e.g., pain management) for the second activity than the existing program. In this way, the medical device may be modified or customized, for example, after being implanted into the patient.

A remote device (e.g., a remote server and/or a remote client) may configure the programming of the medical device. For example, a health professional may remotely or locally generate a new program or programs to improve therapy and transmit (e.g., using the Internet and/or a wireless connection) the new program(s) to the external programmer, e.g., individually or part of a group of programs. In some examples, the remote device may be configured to automatically, or semi-automatically generate the new program to improve therapy, e.g., in response to an event, such as a sensed condition. For example, in response to a change from a first activity (e.g., a patient sitting) to a second activity (e.g., walking), the remote device may generate a new program that may provide more effective therapy (e.g., pain management) for the second activity than the existing program. In this example, the external programmer may configure the medical device with the new program(s) and set the medical device to apply the new program(s) to provide stimulation to provide the improved therapy to the patient. In this way, the medical device may be configured to automatically, or semi-automatically (e.g., with a user input) program the medical device, which may reduce a delay in providing an updated or improved therapy compared to systems that may rely only changes provided by a health professional.

The techniques of this disclosure include a system configured to determine an activity level for the patient based on frequency domain coefficients. For example, the system may sample one or more accelerometer signals. For instance, the system may sample a first accelerometer signal for an accelerometer configured to detect acceleration along a longitudinal axis of the patient (e.g., extending between a foot of a patient to a head of the patient). The system may sample a second accelerometer signal for an accelerometer configured to detect acceleration along a frontal axis of the patient (e.g., extending between shoulders of the patient). In some instances, the system may sample a third accelerometer signal for an accelerometer configured to detect acceleration along a sagittal axis of the patient (e.g., extending between a front of the patient to a back of the patient).

The system may convert the accelerometer information into frequency domain coefficients. For example, the system may convert the accelerometer samples sampled from the first, second, and third accelerometer signals into frequency domain coefficients using a Fourier transform (e.g., a fast Fourier transform (FFT)). In some examples, the system may include dedicated hardware configured to convert the accelerometer information into frequency domain coefficients. Converting the accelerometer information into the frequency domain may allow for a more accurate and/or simplified processing of accelerometer information to determine an activity level compared to systems that only rely on a time domain representation of accelerometer data.

For example, the system may filter out one or more frequency domain coefficients that are outside of a range of frequency. For instance, the system may apply a band pass filter of between 0.75 Hz to 10 Hz to filter out frequency domain coefficients that correspond to acceleration by a car. In some examples, the system may apply a band pass filter of between 15 Hz to 20 Hz to filter out frequency domain coefficients that do not correspond to physical symptom of a patient (e.g., a tremor). In this way, the system may determine an activity level of a patient that is more accurate compared to systems relying only on a time domain representation of accelerometer data. Additionally, higher accuracy in determining an activity level of the patient may allow the system to more accurately determine stimulation parameters (e.g., a program), which may improve a therapy provided to the patient when providing electrical stimulation to the patient compared to systems relying only on a time domain representation of accelerometer data.

Moreover, the system may apply different weights to frequency coefficients associated with different directions. For example, the system may apply a relatively small weight to acceleration along the longitudinal axis of the patient compared to weights for frequency coefficients associated with acceleration along the frontal axis of the patient and/or sagittal axis of the patient. In this way, the system may determine an activity level of a patient that is more accurate compared to systems relying only on a single weight value or no weight values for coefficients associated with acceleration along the longitudinal axis of the patient, the frontal axis of the patient, and the sagittal axis of the patient. Additionally, higher accuracy in determining an activity level of the patient may allow the system to more accurately determine stimulation parameters (e.g., a program), which may improve a therapy provided to the patient when providing electrical stimulation to the patient compared to systems relying only on a single weight value for coefficients associated with acceleration along the longitudinal axis of the patient, the frontal axis of the patient and sagittal axis of the patient.

Techniques described herein may be directed to implantable medical devices and external medical devices. Examples described herein may describe techniques with reference to medical devices, however, aspects of such techniques may apply to any medical device. Again, examples of medical devices, which may be external or implantable), may include drug pumps, insulin pumps, or cardiac stimulation devices, to the extent such medical devices benefit from frequency domain coefficients converted from one or more time domain accelerometer signals.

FIG. 1 is a conceptual diagram illustrating an example system 100 that includes an implantable medical device (IMD) 110 configured to deliver spinal cord stimulation (SCS) therapy and an external programmer 150, in accordance with one or more examples of this disclosure. Although the examples described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of stimulation.

IMD 110 may be configured to provide therapy (e.g., electrical stimulation) using frequency domain coefficients. For example, IMD 110 may itself convert one or more accelerometer signals into frequency domain coefficients. In this example, IMD 110 may determine an activity level (e.g., standing, walking, or laying down) based on the frequency domain coefficients, determine one or more stimulation parameters (e.g., a program) based on the activity level and output electrical stimulation to the patient based on the one or more stimulation parameters. In some examples, external programmer 150 may perform on one or more steps for providing therapy using frequency domain coefficients. For instance, external programmer 150 may perform on or more of: converting one or more accelerometer signals into frequency domain coefficients, determining an activity level, or determining one or more stimulation parameters. In some examples, a remote device may perform on or more of: converting one or more accelerometer signals into frequency domain coefficients, determining an activity level, or determining one or more stimulation parameters.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105, e.g., for relief of chronic pain or other symptoms, or restoration or support of physical function or control in the case of spinal cord injury or degeneration, via one or more electrodes 132A, 132B of leads 130A and/or 130B, respectively. In the example of FIG. 1, each lead 130A, 130B includes eight electrodes 132A, 132B respectively, although the leads may each have a different number of electrodes. Leads 130A, 130B may be referred to collectively as "leads 130" and electrodes 132A, 132B may be referred to collectively as electrodes 132. In other examples, IMD 110 may be coupled to a single lead carrying multiple electrodes or more than two leads each carrying multiple electrodes.

IMD 110 may be a chronic electrical stimulator that remains implanted within patient 105 for weeks, months, or years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to one or more leads percutaneously implanted within the patient. In some examples, IMD 110 uses electrodes on one or more leads, while in other examples, IMD 110 use one or more electrodes on a lead or leads and one of more electrodes on a housing of the IMD. In further examples, IMD 110 may be leadless and instead use only electrodes carried on a housing of IMD.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted at other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

In the example of FIG. 1, electrical stimulation energy, which may be delivered as regulated current or regulated voltage-based pulses, is delivered from IMD 110 to one or more target tissue sites of patient 105 via leads 130 and electrodes 132. Leads 130 position electrodes 132 adjacent to target tissue of spinal cord 120. One or more of the electrodes 32 may be disposed at a distal tip of a lead 130 and/or at other positions at intermediate points along the lead. Leads 130 may be implanted and coupled to IMD 110. The electrodes 132 may transfer electrical stimulation generated by an electrical stimulation generator in IMD 110 to tissue of patient 105. Although leads 130 may each be a single lead, a lead 130 may include a lead extension or other segments that may aid in implantation or positioning of lead 130.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration. Deployment of electrodes via leads 130 is described for purposes of illustration, but electrodes may be arranged on a housing of IMD 110, e.g., in rows and/or columns (or other arrays or patterns), as surface electrodes, ring electrodes, or protrusions.

Stimulation parameters defining the electrical stimulation pulses delivered by IMD 110 through electrodes 132 of leads 130 may include information identifying which electrodes have been selected for delivery of the stimulation pulses according to a stimulation program and the polarities of the selected electrodes (the electrode combination), and voltage or current amplitude, pulse rate (e.g., frequency), and pulse width of the stimulation pulses. The stimulation parameters may further include a cycle parameter that specifies when, or how long, stimulation is turned on and off. Stimulation parameters may be programmed prior to delivery of the stimulation pulses, manually adjusted based on user input, or automatically controlled during delivery of the stimulation pulses, e.g., based on sensed conditions.

Although the example of FIG. 1 is directed to SCS therapy, e.g., to treat pain or restore or support physical function or control in the case of spinal cord injury or degeneration, in other examples, system 100 may be configured to treat other conditions that may benefit from stimulation therapy. For example, system 100 may be used to treat tremor, Parkinson's disease, epilepsy, or other neurological disorders, urinary or fecal incontinence, sexual dysfunction, obesity, or gastroparesis, or psychiatric disorders such as depression, mania, obsessive compulsive disorder, or anxiety disorders. Hence, in some examples, system 100 may be configured to deliver sacral neuromodulation (SNM), deep brain stimulation (DBS), peripheral nerve stimulation (PNS), or other stimulation, such as peripheral nerve field stimulation (PNFS), cortical stimulation (CS), gastrointestinal stimulation, or any other stimulation therapy capable of treating a condition of patient 105.

Leads 130 may include, in some examples, one or more sensors configured to sense one or more physiological parameters of patient 105, such as patient activity, pressure, temperature, or other characteristics. At least some of electrodes 132 may be used to sense electrical signals within patient 105, additionally or alternatively to delivering stimulation. IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions.

Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may reduce the perception of pain by patient 105, and thus, provide efficacious therapy results. In some examples, some electrical stimulation pulses may be directed to glial cells while other electrical stimulation (e.g., delivered by a different electrode combination) is directed to neurons. In other examples, electrical stimulation pulses may be directed to restore a function lost due to a spinal cord injury.

IMD 110 may generate and may deliver electrical stimulation therapy to a target stimulation site within patient 105 via the electrodes of leads 130 to patient 105 according to one or more therapy stimulation programs. A therapy stimulation program specifies values for one or more parameters that define an aspect of the therapy delivered by IMD 110 according to that program. For example, a therapy stimulation program that controls delivery of stimulation by IMD 110 in the form of stimulation pulses may define values for voltage or current pulse amplitude, pulse width, and pulse rate (e.g., pulse frequency) for stimulation pulses delivered by IMD 110 according to that program, as well as the particular electrodes and polarities forming an electrode combination used to deliver the stimulation pulses.

External programmer 150 may transmit therapy stimulation programs, program groups, stimulation parameter adjustments, therapy stimulation program selections, user input, or other information to control the operation of IMD 110, e.g., by wireless telemetry or wired connection. For example, external programmer 150 may configure a complete group or program overwrite. External programmer 150 may perform a stimulation parameter adjustment that changes a set of stimulation parameters of an existing program. For example, external programmer 150 may automatically, semi-automatically, or based on a user selection, may determine or more stimulation parameter adjustments for an existing program. In this example, external programmer 150 may pass through the one or more parameter adjustments for the existing program.

External programmer 150 may be characterized as a physician or clinician programmer if external programmer 150 is primarily intended for use by a physician or clinician. In other cases, external programmer 150 may be characterized as a patient programmer if external programmer 150 is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

IMD 110 and external programmer 150 may exchange information and may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

IMD 110, in response to commands from external programmer 150, may deliver stimulation therapy according to one or more therapy stimulation programs, or a group of programs to a target tissue site of the spinal cord 120 of patient 105 via electrodes 132 on leads 130. In some examples, IMD 110 automatically modifies therapy stimulation programs as therapy needs of patient 105 evolve over time. For example, the modification of the therapy stimulation groups or programs may cause the adjustment of at least one parameter of the plurality of stimulation pulses.

In accordance with the techniques of the disclosure, IMD 110 may be configured to determine an activity level for the patient based on frequency domain coefficients. For example, IMD 110 may sample one or more accelerometer signals. For instance, IMD 110 may sample a first accelerometer signal for an accelerometer configured to detect acceleration along a longitudinal axis of the patient (e.g., extending between a foot of a patient to a head of the patient). IMD 110 may sample a second accelerometer signal for an accelerometer configured to detect acceleration along a frontal axis of the patient (e.g., extending between shoulders of the patient). In some instances, IMD 110 may sample a third accelerometer signal for an accelerometer configured to detect acceleration along a sagittal axis of the patient (e.g., extending between a front of the patient to a back of the patient). As used herein, direction may refer to movement along an axis, for example, a longitudinal axis a frontal axis, or a sagittal axis of the patient.

IMD 110 may convert the accelerometer information into frequency domain coefficients. For example, IMD 110 may convert the accelerometer samples sampled from the first, second, and third accelerometer signals into frequency domain coefficients using a Fourier transform (e.g., a fast Fourier transform (FFT)). In some examples, IMD 110 may include dedicated hardware configured to perform the convert the accelerometer information into frequency domain coefficients. Converting the accelerometer information into the frequency domain may allow for a more accurate and/or simplified processing of accelerometer information to determine an activity level compared to systems that only rely on a time domain representation of accelerometer data.

For example, IMD 110 may apply a band pass filter to filter out one or more frequency domain coefficients that are outside of a range of frequency. For instance, IMD 110 may apply a band pass filter of between 0.75 Hz to 10 Hz to filter out frequency domain coefficients that correspond to acceleration by a car. In some examples, IMD 110 may apply a band pass filter of between 15 Hz to 20 Hz to filter out frequency domain coefficients that do not correspond to physical symptom of a patient (e.g., a tremor). In this way, IMD 110 may determine an activity level of a patient that is more accurate compared to systems relying only on a time domain representation of accelerometer data. Additionally, higher accuracy in determining an activity level of the patient may allow the system to more accurately determine stimulation parameters (e.g., a program), which may improve a therapy provided to the patient when providing electrical stimulation to the patient compared to systems relying only on a time domain representation of accelerometer data.

In some examples, IMD 110 may apply different weights to frequency coefficients associated with different directions. For example, IMD 110 may apply a relatively small weight to acceleration along the longitudinal axis of the patient compared to weights for frequency coefficients associated with acceleration along the frontal axis of the patient and/or sagittal axis of the patient. In this way, IMD 110 may determine an activity level of a patient that is more accurate compared to systems relying only on a single weight value for coefficients associated with acceleration along the longitudinal axis of the patient, the frontal axis of the patient and the sagittal axis of the patient. Additionally, higher accuracy in determining an activity level of the patient may allow IMD 110 to more accurately determine stimulation parameters (e.g., a program), which may improve a therapy provided to the patient when providing electrical stimulation to the patient compared to systems relying only on a single weight value for coefficients associated with acceleration along the longitudinal axis of the patient, the frontal axis of the patient and sagittal axis of the patient.

While in the above examples IMD 110 performs various processes to determine an activity level for the patient based on the frequency domain coefficients, other devices may perform one or more processes described herein for determining an activity level for the patient based on the frequency domain coefficients. For example, external programmer 150 may perform one or more of: sampling one or more accelerometer signals, converting accelerometer information into frequency domain coefficients, applying a filter to the frequency domain coefficients, determining an activity level for the patient based on the frequency domain coefficients, or determining one or more stimulation parameters based on the activity level.

Figure 2:
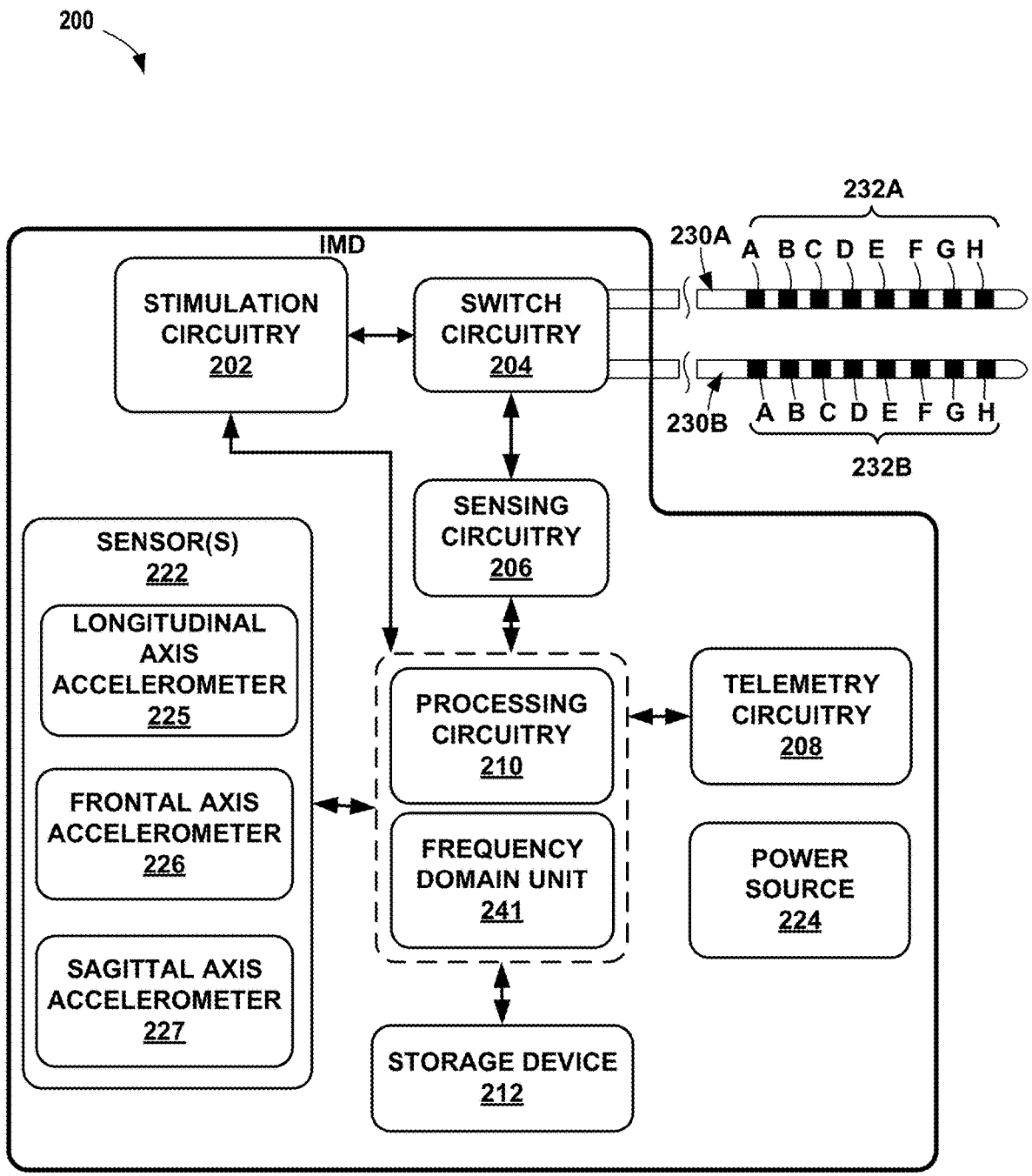
FIG. 2 is a block diagram illustrating an example of an IMD in the form of a stimulation device, in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, power source 224, lead 230A carrying electrodes 232A, which may correspond to lead 130A and electrodes 132A of FIG. 1, and lead 230B carrying electrodes 232B, which may correspond to lead 130B and electrodes 132B of FIG. 1.

Stimulation generation circuitry 202 may generate electrical stimulation pulses selected to alleviate symptoms or dysfunction of one or more diseases, disorders, injuries, or syndromes. While stimulation pulses are described, stimulation signals may take other forms, such as continuous-time signals (e.g., sine waves) or the like. Each of leads 230A, 230B may include any number of electrodes 232A, 232B. In the example of FIG. 2, each set of electrodes 232A, 232B includes eight electrodes A-H. In some examples, the electrodes are arranged in bipolar combinations. A bipolar electrode combination may use electrodes carried by the same lead 230A, 230B or different leads. For example, an electrode A of electrodes 232A may be a cathode and an electrode B of electrodes 232A may be an anode, forming a bipolar combination.

Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232A, 232B, or directed sensed signals from one or more of electrodes 232A, 232B to sensing circuitry 206. In some examples, each of the electrodes 232A, 232B may be associated with respective regulated current source and sink circuitry to selectively and independently configure the electrode to be a regulated cathode or anode, in which case switch circuitry 204 may not be necessary to direct stimulation signals to electrodes. Instead, current sourced or sunk by selected electrodes may be individually controlled. Stimulation generation circuitry 202 and/or sensing circuitry 206 also may include sensing circuitry to direct electrical signals sensed at one or more of electrodes 232A, 232B.

Sensing circuitry 206 may be configured to monitor signals from any combination of electrodes 232A, 232B. In some examples, sensing circuitry 206 includes one or more amplifiers, filters, and analog-to-digital converters. Sensing circuitry 206 may be used to sense electrophysiological signals. In some examples, sensing circuitry 206 detects electrophysiological signals from a particular combination of electrodes 232A, 232B. In some cases, the particular combination of electrodes for sensing electrophysiological signals includes different electrodes than a set of electrodes 232A, 232B used to deliver stimulation pulses. Alternatively, in other cases, the particular combination of electrodes used for electrophysiological sensing includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 may support wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software, or any combination thereof. Processing circuitry 210 controls stimulation generation circuitry 202 to generate stimulation signals according to one or more stimulation parameters and any other instructions stored in storage device 212 to apply the one or more stimulation parameter values, for example, specified by one or more of programs, such as amplitude, pulse width, pulse rate, and pulse shape of each of the stimulation signals.

Frequency domain unit 241 may comprise hardware configured to convert accelerometer information into frequency domain coefficients. For example, frequency domain unit 241 may be configured to apply a window function (e.g., a Hanning window) to accelerometer samples sampled from one or more accelerometer signals to generate one or more data buffers. In some examples, frequency domain unit 241 may be configured to apply a Fourier transform to each one of the one or more data buffers to generate the frequency domain coefficients. For instance, frequency domain unit 241 may be configured to apply a Fourier transform to each one of one or more data buffers generated by frequency domain unit 241. In some instances, frequency domain unit 241 may be configured to apply a Fourier transform to each one of one or more data buffers that are generated by processing circuitry 210 using one or more instructions stored in storage device 212. Frequency domain unit 241 may include one or more processors, such as one or more ASICs, FPGAs, or any other equivalent integrated or discrete logic circuitry, as well as any combinations of such components.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

In accordance with the techniques of the disclosure, processing circuitry 210 may be configured to determine an activity level for the patient based on the frequency domain coefficients. For example, sensors 222 may comprise longitudinal axis accelerometer configured to detect acceleration along a longitudinal axis of the patient (e.g., extending between a foot of a patient to a head of the patient), frontal axis accelerometer 226 configured to detect acceleration along a frontal axis of the patient (e.g., extending between shoulders of the patient), and sagittal axis accelerometer 227 configured to detect acceleration along a sagittal axis of the patient (e.g., extending between a front of the patient to a back of the patient). Processing circuitry 210 may sample one or more accelerometer signals generated by accelerometers 225-227 to generate accelerometer samples. For instance, to generate first accelerometer samples, processing circuitry 210 may sample a first accelerometer signal generated by longitudinal axis accelerometer 225. Processing circuitry 210 may sample a second accelerometer signal generated by frontal axis accelerometer 226. In some instances, processing circuitry 220 may sample a third accelerometer signal generated by sagittal axis accelerometer 227.

Frequency domain unit 241 may apply a window function (e.g., a Hanning window) to accelerometer samples sampled from the one or more accelerometer signals to generate one or more data buffers. While examples below apply a Hanning window as a window function, other window functions may be used. For instance, examples applying a Hanning window may apply a cosine-sum window. For example, frequency domain unit 241 may apply a Hanning window to the first accelerometer samples to generate a first data buffer, apply the Hanning window to the second accelerometer samples to generate a second data buffer, and apply the Hanning window to the third accelerometer samples to generate a third data buffer. In some examples, processing circuitry 210, with one or more instructions, may apply a Hanning window to accelerometer samples sampled from the one or more accelerometer signals to generate one or more data buffers.

Frequency domain unit 241 may apply a Fourier transform to each one of the one or more data buffers to generate the frequency domain coefficients. For example, frequency domain unit 241 may apply a Fourier transform to the first data buffer to generate a first set of frequency domain coefficients, apply the Fourier transform to the second data buffer to generate a second set of frequency domain coefficients, and apply the Fourier transform to the third data buffer to generate a third set of frequency domain coefficients. In some examples, processing circuitry 210, with one or more instructions, may apply the Fourier transform to each one of the one or more data buffers to generate the frequency domain coefficients.

Processing circuitry 210 may filter out one or more frequency domain coefficients that are outside of a range of frequency. In some examples, the frequency range may correspond to a range for human motion. For instance, the frequency range may correspond to an activity comprising one or more of walking or running. An example range for human motion may comprise between 0.75 Hz to 10 Hz. For instance, processing circuitry 210 may apply a band pass filter of between 0.75 Hz to 10 Hz to the first set of frequency domain coefficients, apply the band pass filter to the second set of frequency domain coefficients, and apply the band pass filter to the third set of frequency domain coefficients. In some examples, the frequency range may correspond to physical symptoms for a patient. For instance, the frequency range may correspond to a tremor. An example range for a frequency range corresponding to physical symptoms for a patient may comprise between 15 Hz to 20 Hz. In this way, processing circuitry 210 may determine an activity level of a patient that is more accurate compared to systems relying only on a time domain representation of accelerometer data. Additionally, higher accuracy in determining an activity level of the patient may allow processing circuitry 210 to more accurately determine stimulation parameters (e.g., a program), which may improve a therapy provided to the patient when providing electrical stimulation to the patient compared to systems relying only on a time domain representation of accelerometer data.

In some examples, processing circuitry 210 may apply different weights to frequency coefficients associated with different directions. For example, processing circuitry 210 may determine first activity information based on the first set of the frequency domain coefficients associated with acceleration of the patient along a first direction and determine second activity information based on the second set of the frequency domain coefficients associated with acceleration of the patient along a second direction. In some examples, the first direction is perpendicular to the second direction. For instance, the first direction may be along the longitudinal axis of the patient and the second direction may be along the frontal axis of the patient. In some examples, processing circuitry 210 may determine third activity information based on the third set of the frequency domain coefficients associated with acceleration of the patient along a third direction. In some examples, the third direction is perpendicular to the first direction and to the second direction. For instance, the first direction may be along the longitudinal axis of the patient, the second direction may be along the frontal axis of the patient, and the third direction may be along the sagittal axis of the patient.

Processing circuitry 210 may multiply the first activity information with a first weight value and multiply the second activity information with a second weight value that is different from the first weight value. For example, processing circuitry 210 may multiply the first activity information, which may be associated with acceleration along the longitudinal axis of the patient, with a relatively small weight value and multiply the second activity information with a second weight value with a relatively large weight value. In some examples, processing circuitry 210 may multiply the third activity information with a third weight value that is different from the first weight value and the second weight value. For example, processing circuitry 210 may multiply the third activity information with a third weight value with a relatively large weight value compared to the first weight value. In this way, processing circuitry 210 may apply weights to help determine patient activity using acceleration of the patient associated with human motion (e.g., walking and/or running) rather than non-human motion (e.g., transportation using a car, an elevator, or an escalator), which may improve an accuracy of processing circuitry 210 in determining an activity level for the patient.

While in the above examples IMD 200 performs various processes to determine an activity level for the patient based on the frequency domain coefficients, other devices may perform one or more processes described herein for determining an activity level for the patient based on the frequency domain coefficients. For example, external programmer 150 may perform one or more of: sampling one or more accelerometer signals, converting accelerometer information into frequency domain coefficients, applying a filter to the frequency domain coefficients, determining an activity level for the patient based on the frequency domain coefficients, or determining one or more stimulation parameters based on the activity level.

Figure 3:
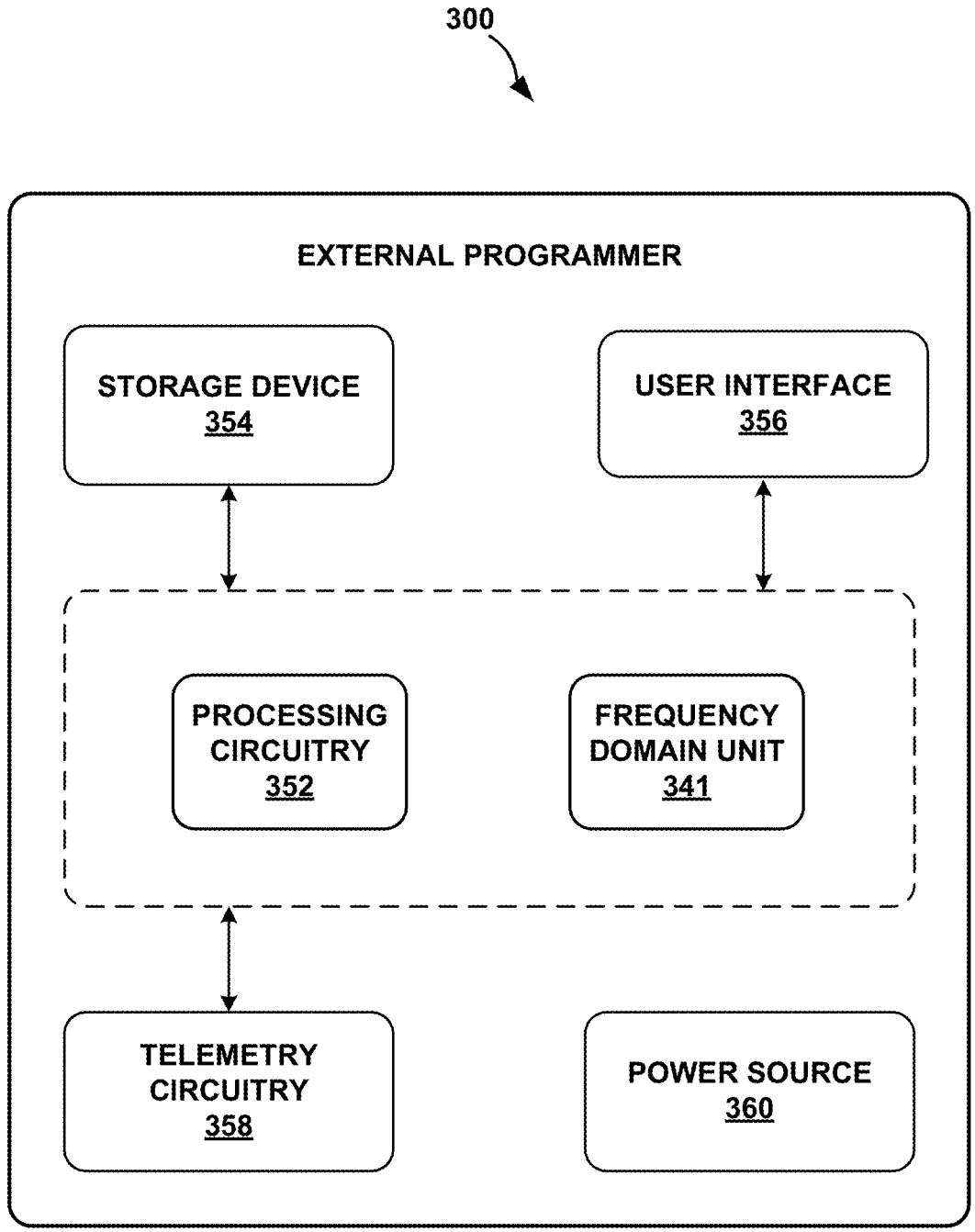
FIG. 3 is a block diagram illustrating an example of an external programmer suitable for use with the IMD of FIG. 2, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352. External programmer 300 may represent a patient programmer, clinician programmer, or another device.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory or receive user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store data recorded at a sensing module of the medical device, and storage device 354 may also store data from one or more sensors of the medical device.

Processing circuitry 352 may be configured to control IMD 110 with a program to provide stimulation. For example, processing circuitry 352 may automatically or semi-automatically set or adjust programs at IMD 110 by transmitting, with telemetry circuitry 358, instructions to IMD 110. For instance, in response to a change (e.g., a change indicated by user input, a change sensed by IMD 110, etc.) in activity of a patient (e.g., standing, walking, voiding, etc.), processing circuitry 352 may automatically or semi-automatically set or adjust programs at IMD 110. For instance, processing circuitry 352 may, in response to determining that the patient would not like to void, output instructions to IMD 110 to use a first group stored at IMD 110 for controlled voiding. In this instance, processing circuitry 352 may, in response to determining that the patient would like to void, output instructions to IMD 110 to use a new group or program stored at IMD 110 for controlled voiding.

Frequency domain unit 341 may comprise hardware configured to convert accelerometer information into frequency domain coefficients. For example, frequency domain unit 341 may be configured to apply a window function (e.g., a Hanning window) to accelerometer samples sampled from one or more accelerometer signals to generate one or more data buffers. In some examples, frequency domain unit 341 may be configured to apply a Fourier transform to each one of the one or more data buffers to generate the frequency domain coefficients. For instance, frequency domain unit 341 may be configured to apply a Fourier transform to each one of one or more data buffers generated by frequency domain unit 241. In some instances, frequency domain unit 341 may be configured to apply a Fourier transform to each one of one or more data buffers that are generated by processing circuitry 352 using one or more instructions. Frequency domain unit 341 may include one or more processors, such as one or more ASICs, FPGAs, or any other equivalent integrated or discrete logic circuitry, as well as any combinations of such components.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, or the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

In accordance with the techniques of the disclosure, processing circuitry 352 may be configured to determine an activity level for the patient based on the frequency domain coefficients. Processing circuitry 352 may sample one or more accelerometer signals generated by accelerometers (e.g., accelerometers 225-227 of IMD 200) to generate accelerometer samples. For instance, to generate first accelerometer samples, processing circuitry 352 may sample a first accelerometer signal generated by longitudinal axis accelerometer 225. Processing circuitry 352 may sample a second accelerometer signal generated by frontal axis accelerometer 226. In some instances, processing circuitry 352 may sample a third accelerometer signal generated by sagittal axis accelerometer 227.

Frequency domain unit 341 may apply a window function (e.g., a Hanning window) to accelerometer samples sampled from the one or more accelerometer signals to generate one or more data buffers. While examples below apply a Hanning window as a window function, other window functions may be used. For instance, examples applying a Hanning window may apply a cosine-sum window. For example, frequency domain unit 341 may apply a Hanning window to the first accelerometer samples to generate a first data buffer, apply the Hanning window to the second accelerometer samples to generate a second data buffer, and apply the Hanning window to the third accelerometer samples to generate a third data buffer. In some examples, processing circuitry 352, with one or more instructions, may apply a Hanning window to accelerometer samples sampled from the one or more accelerometer signals to generate one or more data buffers.

Frequency domain unit 341 may apply a Fourier transform to each one of the one or more data buffers to generate the frequency domain coefficients. For example, frequency domain unit 341 may apply a Fourier transform to the first data buffer to generate a first set of frequency domain coefficients, apply the Fourier transform to the second data buffer to generate a second set of frequency domain coefficients, and apply the Fourier transform to the third data buffer to generate a third set of frequency domain coefficients. In some examples, processing circuitry 352, with one or more instructions, may apply the Fourier transform to each one of the one or more data buffers to generate the frequency domain coefficients.

Processing circuitry 352 may filter out one or more frequency domain coefficients that are outside of a range of frequency. In some examples, the frequency range may correspond to a range for human motion. In some examples, the frequency range may correspond to physical symptoms for a patient. In this way, processing circuitry 352 may determine an activity level of a patient that is more accurate compared to systems relying only on a time domain representation of accelerometer data. Additionally, higher accuracy in determining an activity level of the patient may allow processing circuitry 352 to more accurately determine stimulation parameters (e.g., a program), which may improve a therapy provided to the patient when providing electrical stimulation to the patient compared to systems relying only on a time domain representation of accelerometer data.

In some examples, processing circuitry 352 may apply different weights to frequency coefficients associated with different directions. For example, processing circuitry 352 may determine first activity information based on the first set of the frequency domain coefficients associated with acceleration of the patient along a first direction and determine second activity information based on the second set of the frequency domain coefficients associated with acceleration of the patient along a second direction. In some examples, the first direction is perpendicular to the second direction. For instance, the first direction may be along the longitudinal axis of the patient and the second direction may be along the frontal axis of the patient. In some examples, processing circuitry 352 may determine third activity information based on the third set of the frequency domain coefficients associated with acceleration of the patient along a third direction. In some examples, the third direction is perpendicular to the first direction and to the second direction. For instance, the first direction may be along the longitudinal axis of the patient, the second direction may be along the frontal axis of the patient, and the third direction may be along the sagittal axis of the patient.

Processing circuitry 352 may multiply the first activity information with a first weight value and multiply the second activity information with a second weight value that is different from the first weight value. For example, processing circuitry 352 may multiply the first activity information, which may be associated with acceleration along the longitudinal axis of the patient, with a relatively small weight value and multiply the second activity information with a second weight value with a relatively large weight value. In some examples, processing circuitry 352 may multiply the third activity information with a third weight value that is different from the first weight value and the second weight value. For example, processing circuitry 352 may multiply the third activity information with a third weight value with a relatively large weight value compared to the first weight value. In this way, processing circuitry 352 may apply weights to help determine patient activity using acceleration of the patient associated with human motion (e.g., walking and/or running) rather than non-human motion (e.g., transportation using a car, an elevator, or an escalator), which may improve an accuracy of processing circuitry 352 in determining an activity level for the patient.

While in the above examples external programmer 300 performs various processes to determine an activity level for the patient based on the frequency domain coefficients, other devices may perform one or more processes described herein for determining an activity level for the patient based on the frequency domain coefficients. For example, IMD 110 may perform one or more of: sampling one or more accelerometer signals, converting accelerometer information into frequency domain coefficients, applying a filter to the frequency domain coefficients, determining an activity level for the patient based on the frequency domain coefficients, or determining one or more stimulation parameters based on the activity level.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
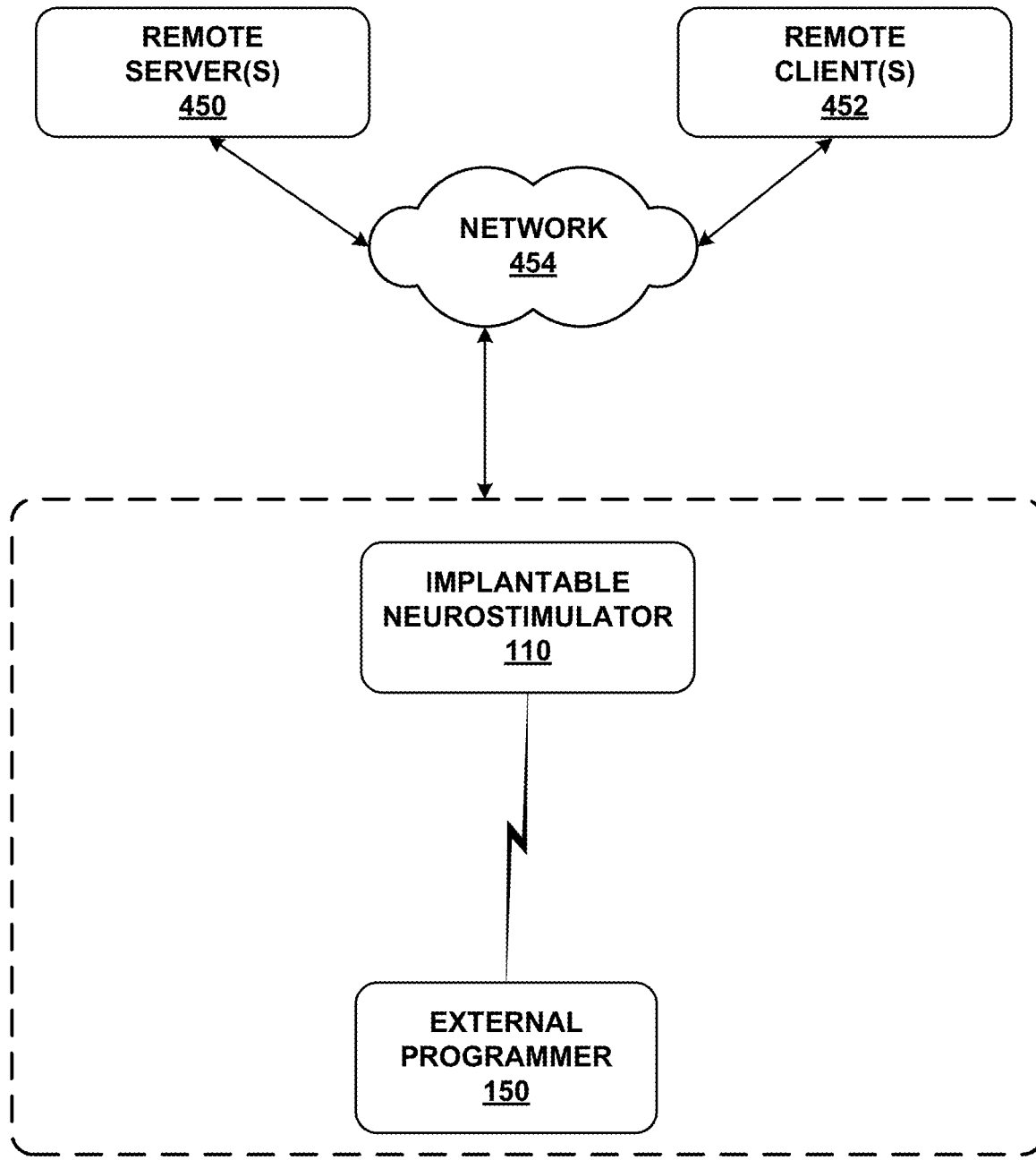
FIG. 4 is a block diagram illustrating an example of one or more remote servers and one or more remote clients suitable for use with the IMD of FIG. 1, in accordance with one or more techniques of this disclosure.

FIG. 4 is a block diagram illustrating an example of one or more remote servers 450 (referred to herein as "remote server 450") and one or more remote clients 452 (referred to herein as "remote clients 452") suitable for use with the IMB of FIG. 1, in accordance with one or more techniques of this disclosure. Remote server 450 may represent a cloud computing infrastructure. Remote client 452 may represent a clinician device geographically remote from external programmer 150 and/or IMD 110. For instance, remote client 452 may be used by a health professional at a doctor's office and the patient and IMD 110 may be at a home of the patient. Remote server 450 and/or remote client 452 may be referred to herein as a remote device. Network 454 may comprise one or more wired (e.g., Ethernet) and/or wireless networks (e.g., Wi-Fi™, Bluetooth™, Zigbee™, IEEE 802.11, etc.). In some examples, network 454 may comprise the Internet.

A remote device (e.g., remote server 450 and/or remote client 452) may be configured to control IMD 110 with a program or a group of programs to provide stimulation. For example, the remote device may automatically or semi-automatically set or adjust programs at IMD 110. For instance, in response to a change in activity of a patient (e.g., standing, walking, voiding, etc.), the remote device may automatically or semi-automatically set or adjust programs at IMD 110. For instance, the remote device may receive sensor information or user input information from IMD 110 or external programmer 150 via the network 454 that indicates a change in activity of the patient.

In accordance with the techniques of the disclosure, remote client 452 may be configured to determine an activity level for the patient based on frequency domain coefficients. Remote client 452 may sample one or more accelerometer signals generated by accelerometers (e.g., accelerometers 225-227 of IMD 200) to generate accelerometer samples. For instance, to generate first accelerometer samples, remote client 452 may sample a first accelerometer signal generated by longitudinal axis accelerometer 225. Remote client 452 may sample a second accelerometer signal generated by frontal axis accelerometer 226. In some instances, remote client 452 may sample a third accelerometer signal generated by sagittal axis accelerometer 227.

Remote client 452 may apply, with a frequency domain unit or without a frequency domain unit, a window function (e.g., a Hanning window) to accelerometer samples sampled from the one or more accelerometer signals to generate one or more data buffers. While examples below apply a Hanning window as a window function, other window functions may be used. For instance, examples applying a Hanning window may apply a cosine-sum window. For example, remote client 452 may apply a Hanning window to the first accelerometer samples to generate a first data buffer, apply the Hanning window to the second accelerometer samples to generate a second data buffer, and apply the Hanning window to the third accelerometer samples to generate a third data buffer.

Remote client 452 may apply, with a frequency domain unit or without a frequency domain unit, a Fourier transform to each one of the one or more data buffers to generate the frequency domain coefficients. For example, remote client 452 may apply a Fourier transform to the first data buffer to generate a first set of frequency domain coefficients, apply the Fourier transform to the second data buffer to generate a second set of frequency domain coefficients, and apply the Fourier transform to the third data buffer to generate a third set of frequency domain coefficients.

Remote client 452 may filter out one or more frequency domain coefficients that are outside of a range of frequency. In some examples, the frequency range may correspond to a range for human motion. In some examples, the frequency range may correspond to physical symptoms for a patient. In this way, remote client 452 may determine an activity level of a patient that is more accurate compared to systems relying only on a time domain representation of accelerometer data. Additionally, higher accuracy in determining an activity level of the patient may allow remote client 452 to more accurately determine stimulation parameters (e.g., a program), which may improve a therapy provided to the patient when providing electrical stimulation to the patient compared to systems relying only on a time domain representation of accelerometer data.

In some examples, remote client 452 may apply different weights to frequency coefficients associated with different directions. For example, remote client 452 may determine first activity information based on the first set of the frequency domain coefficients associated with acceleration of the patient along a first direction and determine second activity information based on the second set of the frequency domain coefficients associated with acceleration of the patient along a second direction. In some examples, the first direction is perpendicular to the second direction. For instance, the first direction may be along the longitudinal axis of the patient and the second direction may be along the frontal axis of the patient. In some examples, remote client 452 may determine third activity information based on the third set of the frequency domain coefficients associated with acceleration of the patient along a third direction. In some examples, the third direction is perpendicular to the first direction and to the second direction. For instance, the first direction may be along the longitudinal axis of the patient, the second direction may be along the frontal axis of the patient, and the third direction may be along the sagittal axis of the patient.

Remote client 452 may multiply the first activity information with a first weight value and multiply the second activity information with a second weight value that is different from the first weight value. For example, remote client 452 may multiply the first activity information, which may be associated with acceleration along the longitudinal axis of the patient, with a relatively small weight value and multiply the second activity information with a second weight value with a relatively large weight value. In some examples, remote client 452 may multiply the third activity information with a third weight value that is different from the first weight value and the second weight value. For example, remote client 452 may multiply the third activity information with a third weight value with a relatively large weight value compared to the first weight value. In this way, remote client 452 may apply weights to help determine patient activity using acceleration of the patient associated with human motion (e.g., walking and/or running) rather than non-human motion (e.g., transportation using a car, an elevator, or an escalator), which may improve an accuracy of remote client 452 in determining an activity level for the patient.

While in the above examples remote client 452 performs various processes to determine an activity level for the patient based on the frequency domain coefficients, other devices may perform one or more processes described herein for determining an activity level for the patient based on the frequency domain coefficients. For example, one or more of remote server 450, external programmer 150, or IMD 110 may perform one or more of: sampling one or more accelerometer signals, converting accelerometer information into frequency domain coefficients, applying a filter to the frequency domain coefficients, determining an activity level for the patient based on the frequency domain coefficients, or determining one or more stimulation parameters based on the activity level. Although shown as separate entities, in some examples, functionality may be distributed differently than that shown in FIG. 4. For example, remote server 450 and remote client 452 may be the same system.

Figure 5:
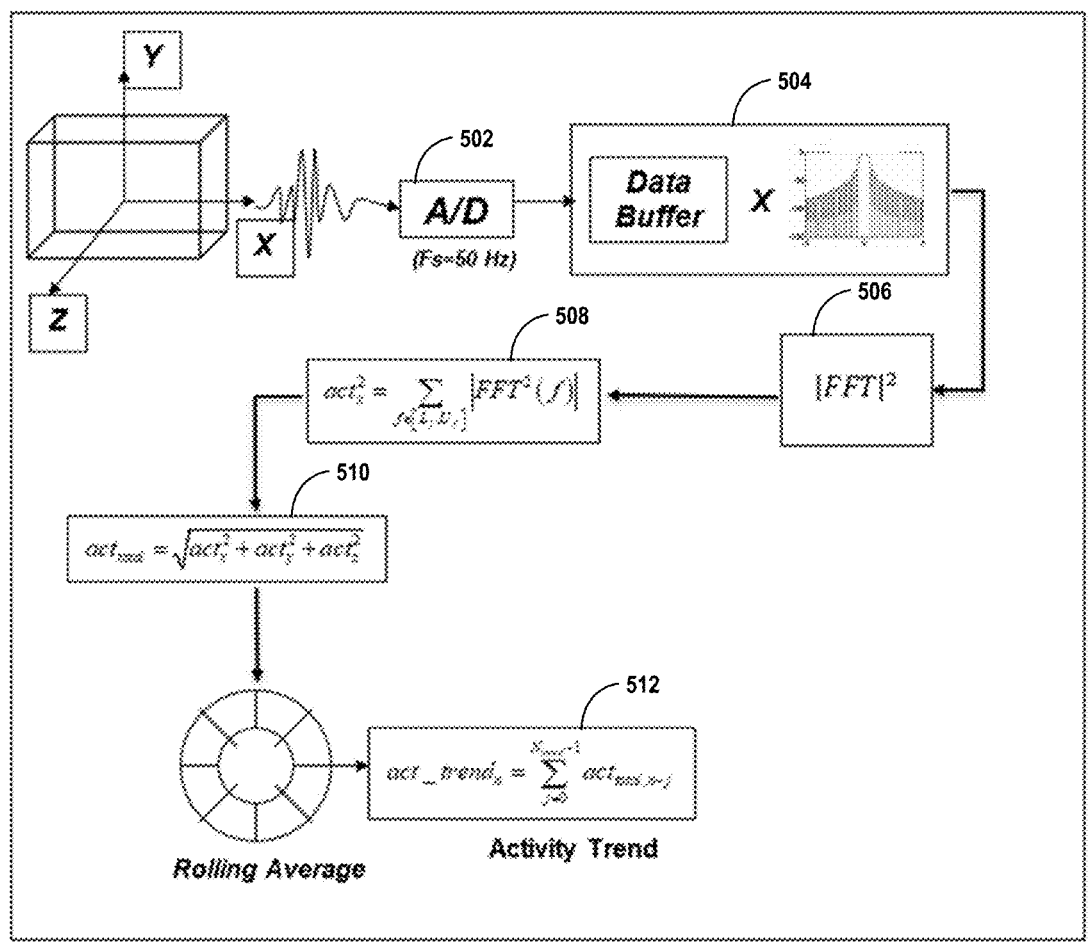
FIG. 5 is a conceptual diagram of determining an activity level using frequency domain coefficients, in accordance with one or more techniques of this disclosure.

FIG. 5 is a conceptual diagram of determining an activity level using frequency domain coefficients, in accordance with one or more techniques of this disclosure. For example, IMD 110 may sample (e.g., at 50 Hz), using an A/D converter, signals output from one or more accelerometers (e.g., accelerometers 225-227) tracking an acceleration in each of an x, y, and z direction to generate respective data buffers along each of the x, y, and z directions (502). Rather than processing the data buffers in the time domain, which may be computationally intensive, techniques described herein may apply a Fourier transform that translates the data buffers from a time domain to a frequency domain.

For example, IMD 110 may include hardware (e.g., frequency domain unit 241) configured to apply, for each of the x, y, and z directions, a Hanning window to the data buffer (504) and determine squared FFT (e.g., $|FFT|^2$) coefficients for a set of frequency bins (506). While this example applies a Hanning window as a window function, other window functions may be used. IMD 110 may calculate activity information (508) along one or more of the x, y, and z directions. For example, IMD 110 may calculate one or more of equations 1-3.

$$act_x^2 = \Sigma_{f \in [L_f, U_f]} |FFT_x^2(f)| \quad \text{Equation 1}$$

where $act^2_x$ is an activity level along an x-direction, f is frequency, $L_f$ is a lower frequency limit, $U_f$ is an upper frequency limit, and $|FFT_x^2(f)|$ is the frequency domain coefficients for the x-direction.

For instance, IMD 110 may apply spectral processing, leveraging FFT hardware to implement overlapping windowed periodograms and integrate the periodograms over a frequency range relevant for human motion. The set of frequency bins may be limited to a lower frequency limit ($L_f$) of about 0.75 Hz and an upper frequency limit ($U_f$) of about 10 Hz. IMD 110 may calculate frequency coefficients for the y-direction and/or the z-direction. For example, IMD 110 may calculate equation 2.

$$act_y^2 = \Sigma_{f \in [L_f, U_f]} |FFT_y^2(f)| \quad \text{Equation 2}$$

where $act^2_y$ is an activity level along an y-direction, f is frequency, $L_f$ is a lower frequency limit, $U_f$ is an upper frequency limit, and $|FFT_y^2(f)|$ is the frequency domain coefficients for the y-direction.

Similarly, IMD 110 may calculate equation 3.

$$act_z^2 = \Sigma_{f \in [L_f, U_f]} |FFT_z^2(f)| \quad \text{Equation 3}$$

where $act^2_z$ is an activity level along a z-direction, f is frequency, $L_f$ is a lower frequency limit, $U_f$ is an upper frequency limit, and $|FFT_z^2(f)|$ is the frequency domain coefficients for the z-direction.

IMD 110 may apply a square root function to a sum of the magnitude squared FFT coefficients to generate an instant activity level (510). For example, IMD 110 may calculate equation 4.

$$act_{total}(t) = \sqrt{act_x^2 + act_y^2 + act_z^2} \quad \text{Equation 4}$$

where $act_{total}(t)$ is an instant activity level at time 't', $act^2_x$ is an activity level along a x-direction, $act^2_y$ is an activity level along an y-direction, and $act^2_z$ is an activity level along a z-direction.

In some examples, IMD 110 may apply weights to the x, y, and z axes of the accelerometer to tailor the activity information for a particular patient. For example, activity along a lateral and medial direction (e.g., along the frontal axis of the patient) may be used to determine a sway in a patient. For example, IMD 110 may calculate equation 5.

$$act_{total}(t) = \sqrt{W_x * act_x^2 + W_y * act_y^2 * W_z * act_z^2} \quad \text{Equation 5}$$

where $act_{total}(t)$ is an instant activity level at time 't', $W_x$ is a first weight value for the x-direction, $W_y$ is a second weight value for the y-direction, and $W_z$ is a third weight value for the z-direction.

IMD 110 may apply a rolling average to two or more instant activity levels to generate the activity level (512). For example, IMD 110 may average two or more instant activity levels. For instance, IMD 110 may calculate equation 6.

$$act_{trend_n} = \sum_{j=0}^{N_{trend}-1} act_{total, n-j} \quad \text{Equation 6}$$

where $act\_trend_n$ is the activity level and $N_{trend}$ is a number of instant activity levels for a rolling average.

The techniques described above may enable customization of therapy for patients. For example, because a processing of the accelerometer data is in the frequency domain instead of the time domain, IMD 110 may limit a frequency range to be within a physiological range (or ranges) of frequencies for a specific patient, thereby excluding information that is not representative of activity. For example, by limiting the frequency range, IMD 110 may help to eliminate or reduce artifacts (e.g., car rides) that may provide misleading information regarding activity level. Elimination or reduction of such artifacts may increase an accuracy of the determined activity level compared to devices using a time domain activity technique. Further, IMD 110 may limit the frequency range to a desired activity (e.g., walking or running) and/or to detect physical symptoms (e.g., falls, tremors, seizures, etc.). In some examples, limiting the frequency range may provide an activity level that corresponds to a step count for the patient, which may provide valuable information about a patient's activity level.

While in the above examples IMD 110 performs various processes to determine an activity level for the patient based on the frequency domain coefficients, other devices may perform one or more processes described herein for determining an activity level for the patient based on the frequency domain coefficients. For example, one or more of remote server 450, remote client 452, or external programmer 150 may perform one or more of: sampling one or more accelerometer signals, converting accelerometer information into frequency domain coefficients, applying a filter to the frequency domain coefficients, determining an activity level for the patient based on the frequency domain coefficients, or determining one or more stimulation parameters based on the activity level.

Figure 6:
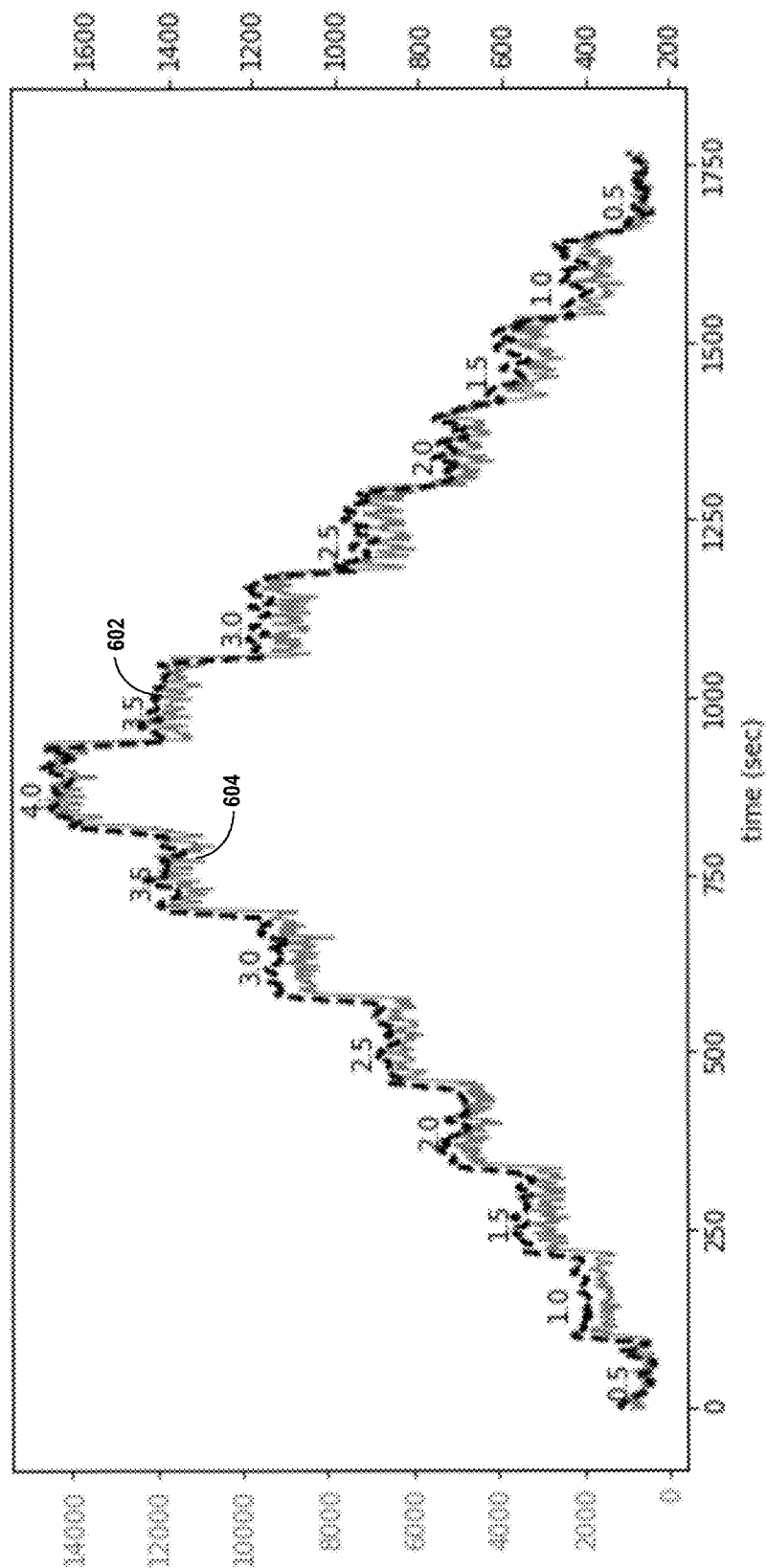
FIG. 6 is a plot diagram illustrating an example of activity levels, in accordance with one or more techniques of this disclosure.

FIG. 6 is a plot diagram illustrating an example of activity levels, in accordance with one or more techniques of this disclosure. The activity level 602 is generated using techniques described herein using frequency domain coefficients and reference activity level 604 is generated using only time domain coefficients. In this example, a treadmill has 15 two minute stages with the first 8 stages increasing from 0.5 mph to 4.0 mph in 0.5 mph increments at 1% grade followed by 7 stages decreasing from 3.5 mph to 0.5 mph. As shown, activity level 602 provides a less noisy activity level that more accurately represents a constant activity level during each respective 2 minute stage compared to reference activity level 604.

Figure 7:
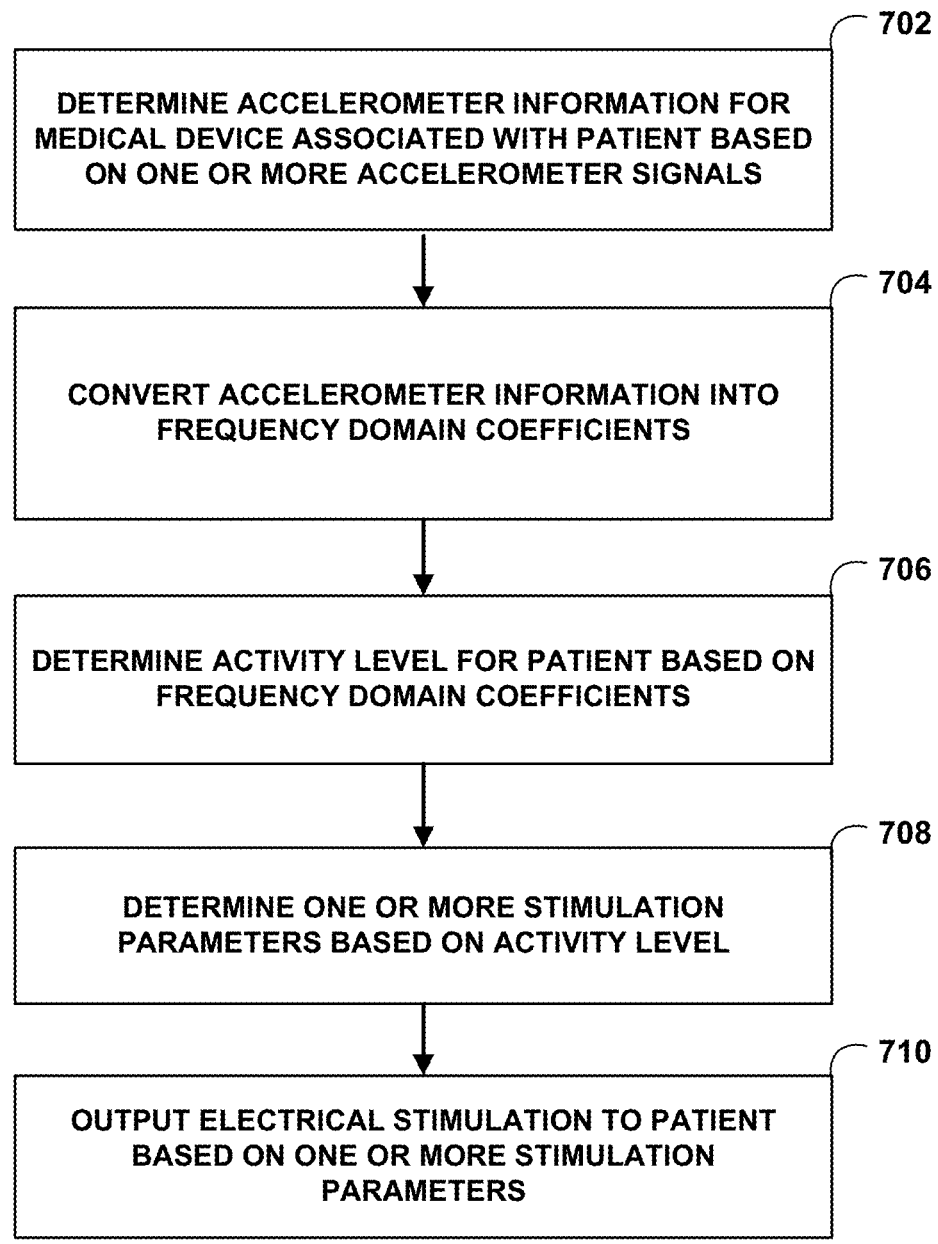
FIG. 7 is a flow diagram illustrating a process for providing stimulation to a patient using frequency domain coefficients, in accordance with one or more techniques of this disclosure.

FIG. 7 is a flow diagram illustrating a process for providing stimulation to a patient using frequency domain coefficients, in accordance with one or more techniques of this disclosure. FIG. 7 is discussed with reference to FIGS. 1-6 for example purposes only. In the following example, IMD 110 performs 702-710 of FIG. 7. However, in other examples, other devices may perform the process of FIG. 7 as explained in further detail below. In the following examples, IMD 110 is used as a medical device. However, in some examples, an external medical device may be used instead of IMD 110.

A medical device (e.g., IMD 110) may determine accelerometer information for a medical device associated with a patient based on the one or more accelerometer signals (702). For example, processing circuitry 210 (or more specifically an analog-to-digital converter of processing circuitry 210) may sample one or more accelerometer signals generated by accelerometers 225-227 to generate the accelerometer information.

The medical device (e.g., IMD 110) may convert the accelerometer information into frequency domain coefficients (704). For example, frequency domain unit 241 may apply a window function (e.g., a Hanning window) to accelerometer samples sampled from the one or more accelerometer signals to generate one or more data buffers. In this example, frequency domain unit 241 may apply a Fourier transform (e.g., a FFT) to each one of the one or more data buffers to generate the frequency domain coefficients.

The medical device (e.g., IMD 110) may determine an activity level for the patient based on the frequency domain coefficients (706). For example, IMD 110 may apply equations 1-4, and 6 to determine the activity level. In some examples, IMD 110 may apply equations 1-3,5, and 6 to determine the activity level.

The medical device (e.g., IMD 110) may determine one or more stimulation parameters based on the activity level (708). For example, IMD 110 may select a patient activity from a plurality of patient activities based on the activity level. The plurality of patient activities may comprise one or more of laying down, upright, or walking. For instance, laying down may be assigned an activity level of less than 'a', upright may be assigned an activity level of 'a' through and walking may be assigned an activity level of greater than 'W'. In this example, IMD 110 may select a program from the plurality of programs of simulation parameters based on the patient activity. For instance, in response to determining that the activity level is within the activity level for upright (e.g., 'a' through 'b'), IMD 110 may select a program for upright. In response, however, to determining that the activity level is less than the activity level for upright (e.g., 'a' through 'b'), IMD 110 may select a program for laying down. Similarly, in response to determining that the activity level is greater than the activity level for upright (e.g., 'a' through 'b'), IMD 110 may select a program for walking.

The medical device (e.g., IMD 110) may output electrical stimulation to the patient based on the one or more stimulation parameters (710). For example, IMD 110 may apply electrical stimulation with one or more of a voltage amplitude, a current amplitude, a pulse rate (e.g., frequency), or a pulse width corresponding to the one or more stimulation parameters.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry. Accordingly, the terms "processor" and "processing circuitry," as used herein may refer to any of the foregoing structures or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

What is claimed is:

1. A system for providing stimulation to a patient, the system comprising:
   one or more accelerometers configured to generate one or more accelerometer signals; and
   one or more processors implemented in circuitry, the one or more processors being configured to:
   determine accelerometer information for a medical device associated with the patient based on the one or more accelerometer signals;
   convert the accelerometer information into a first set of frequency domain coefficients associated with acceleration of the patient along a longitudinal axis of the patient, a second set of frequency domain coefficients associated with acceleration of the patient along a frontal axis of the patient, and a third set of frequency domain coefficients associated with acceleration of the patient along a sagittal axis of the patient;
   filter out one or more frequency domain coefficients of the first set of frequency domain coefficients that are outside of a frequency range to generate an activity level along the longitudinal axis;
   filter out one or more frequency domain coefficients of the second set of frequency domain coefficients that are outside of the frequency range to generate an activity level along the frontal axis;
   filter out one or more frequency domain coefficients of the third set of frequency domain coefficients that are outside of the frequency range to generate an activity level along the sagittal axis;
   generate a total activity level for the patient based on the activity level along the longitudinal axis, a first weight value for the activity level along the longitudinal axis, the activity level along the frontal axis, a second weight value for the activity level along the frontal axis, the activity level along the sagittal axis, and a third weight value for the activity level along the sagittal axis, wherein the first weight value for the activity level along the longitudinal axis is less than the second weight value and the third weight value;
   select a patient activity from a plurality of patient activities based on the total activity level;
   select a program from a plurality of programs of stimulation parameters based on the selected patient activity; and
   output electrical stimulation to the patient based on the stimulation parameters of the selected program.

2. The system of claim 1, wherein, to convert the accelerometer information, the one or more processors are configured to:
   apply a window function to accelerometer samples sampled from the one or more accelerometer signals to generate one or more data buffers; and
   generate the first set of frequency domain coefficients based on the one or more data buffers.

3. The system of claim 2, wherein, to generate the first set of frequency domain coefficients, the one or more processors are configured to:
   apply a Fourier transform to each one of the one or more data buffers to generate the first set of frequency domain coefficients.

4. The system of claim 3, wherein the one or more processors comprise a frequency domain unit implemented in the circuitry and arranged in the medical device and configured to apply the window function to the accelerometer samples, apply the Fourier transform to the data buffer, or apply the window function to the accelerometer samples and apply the Fourier transform to the data buffer.

5. The system of claim 1, wherein the frequency range comprises 0.75 Hz to 10 Hz.

6. The system of claim 1, wherein the frequency range corresponds to an activity for the patient, and wherein the activity comprises one or more of walking or running.

7. The system of claim 1, wherein, to select the patient activity, the one or more processors are configured to:
   determine a rolling average of the total activity level; and
   select the patient activity based on the determined rolling average.

8. The system of claim 1, wherein the one or more processors and the one or more accelerometers are arranged in the medical device.

9. The system of claim 1, wherein at least one of the one or more processors is arranged in an external programmer associated with the medical device, at least one of the one or more processors is arranged in a remote device, or at least one of the one or more processors is arranged in the external programmer associated with the medical device and at least one of the one or more processors is arranged in the remote device.

10. The system of claim 1, wherein the plurality of patient activities comprises one or more of sitting, standing, walking, running, voiding, or laying down.

11. A method for providing stimulation to a patient, the method comprising:
   determining, by processing circuitry implemented using one or more processors, accelerometer information for a medical device associated with the patient based on one or more accelerometer signals generated by one or more accelerometers;
   converting, by the processing circuitry, the accelerometer information into a first set of frequency domain coefficients associated with acceleration of the patient along a longitudinal axis of the patient, a second set of frequency domain coefficients associated with acceleration of the patient along a frontal axis of the patient, and a third set of frequency domain coefficients associated with acceleration of the patient along a sagittal axis of the patient;

filtering, by the processing circuitry, out one or more frequency domain coefficients of the first set of frequency domain coefficients that are outside of a frequency range to generate an activity level along the longitudinal axis;

filtering, by the processing circuitry, out one or more frequency domain coefficients of the second set of frequency domain coefficients that are outside of the frequency range to generate an activity level along the frontal axis;

filtering, by the processing circuitry, out one or more frequency domain coefficients of the third set of frequency domain coefficients that are outside the frequency range to generate an activity level along the sagittal axis;

generating, by the processing circuitry, a total activity level for the patient based on the activity level along the longitudinal axis, a first weight value for the activity level along the longitudinal axis, the activity level along the frontal axis, a second weight value for the activity level along the frontal axis, the activity level along the sagittal axis, and a third weight value for the activity level along the sagittal axis, wherein the first weight value for the activity level along the longitudinal axis is less than the second weight value and the third weight value;

selecting, by the processing circuitry, a patient activity from a plurality of patient activities based on the total activity level;

selecting, by the processing circuitry, a program from a plurality of programs of stimulation parameters based on the selected patient activity; and outputting, by the processing circuitry, electrical stimulation to the patient based on the stimulation parameters of the selected program.

12. A medical device for providing stimulation to a patient, the medical device comprising processing circuitry implemented using one or more processors, a frequency domain unit implemented in the circuitry, and one or more accelerometers configured to generate one or more accelerometer signals, wherein the processing circuitry is configured to determine accelerometer information based on the one or more accelerometer signals;

wherein the frequency domain unit is configured to convert the accelerometer information into a first set of frequency domain coefficients associated with acceleration of the patient along a longitudinal axis of the patient, a second set of frequency domain coefficients associated with acceleration of the patient along a frontal axis of the patient, and a third set of frequency domain coefficients associated with acceleration of the patient along a sagittal axis of the patient; and wherein the processing circuitry is further configured to:
filter out one or more frequency domain coefficients of the first set of frequency domain coefficients that are outside of a frequency range to generate an activity level along the longitudinal axis of the patient;

filter out one or more frequency domain coefficients of the second set of frequency domain coefficients that are outside of the frequency range to generate an activity level along the frontal axis of the patient;

filter out one or more frequency domain coefficients of the second set of frequency domain coefficients that are outside of the frequency range to generate an activity level along the sagittal axis of the patient;

generate a total activity level for the patient based on the activity level along the longitudinal axis, a first weight value for the activity level along the longitudinal axis, the activity level along the frontal axis, a second weight value for the activity level along the frontal axis, the activity level along the sagittal axis, and a third weight value for the activity level along the sagittal axis, wherein the first weight value for the activity level along the longitudinal axis is less than the second weight value and the third weight value;

select a patient activity from a plurality of patient activities based on the total activity level;

select a program from a plurality of programs of stimulation parameters based on the selected patient activity; and output electrical stimulation to the patient based on the stimulation parameters of the program.

* * * * *